(12) United States Patent
Yamka et al.

(10) Patent No.: US 9,420,808 B2
(45) Date of Patent: *Aug. 23, 2016

(54) COMPOSITIONS AND METHODS FOR INCREASING LEAN MUSCLE MASS AND/OR REDUCING FAT GAIN

(75) Inventors: Ryan Michael Yamka, Topeka, KS (US); Kim Gene Friesen, Carthage, IN (US); Steven Curtis Zicker, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 909 days.

This patent is subject to a terminal disclaimer.

(21) Appl. No.: 13/274,597

(22) Filed: Oct. 17, 2011

(65) Prior Publication Data

US 2012/0031785 A1  Feb. 9, 2012

Related U.S. Application Data

(62) Division of application No. 12/091,757, filed as application No. PCT/US2006/060249 on Oct. 26, 2006, now Pat. No. 8,071,122.

(60) Provisional application No. 60/730,346, filed on Oct. 26, 2005.

(51) Int. Cl.
| | |
|---|---|
| *A23K 1/16* | (2006.01) |
| *A23K 1/18* | (2006.01) |
| *A23L 1/305* | (2006.01) |

(52) U.S. Cl.
CPC .............. *A23K 1/1634* (2013.01); *A23K 1/1846* (2013.01); *A23L 1/3051* (2013.01); *A23V 2002/00* (2013.01)

(58) Field of Classification Search
None
See application file for complete search history.

(56) References Cited

U.S. PATENT DOCUMENTS

| 6,221,836 B1 | 4/2001 | Beale et al. |
| 2003/0224496 A1 | 12/2003 | Jakel et al. |
| 2004/0081743 A1 | 4/2004 | Laflamme et al. |

FOREIGN PATENT DOCUMENTS

| EP | 0728418 | 8/1996 |
| WO | WO 2006/105112 | 10/2006 |

OTHER PUBLICATIONS

Hill's Pet Nutrition, Inc., "The Leaders in Pet Nutrition and Innovation", Internet Article, 2007.
Henry, Y. et al., "Effect of Dietary Level of Lysine and of Level and Source of Protein on Feed Intake, Growth Performance, and Plasma Amino Acid Pattern in the Finishing Pig"; J. Anim. Scit (1992) 70:188-195.
Dzanis, David a., "The Association of American Feed Control Officials Dog and Cat Food Nutrient Profiles: Substantiation of Nutrition Adequacy of Complete and Balanced Pet Foods in the United States," Nutrition Through the Cell Life Cycle (1994) pp. 2535S - 2539S.

*Primary Examiner* — Paul Zarek

(57) ABSTRACT

Compositions and methods for increasing lean muscle mass and/or reducing fat gain in growing animals by feeding the animals a composition having a total lysine to metabolizable energy ratio of from about 2.5 to about 6 g/Mcal and comprising (a) arginine in a total arginine to total lysine ratio of from about 1.1 to about 1.6; (b) isoleucine in a total isoleucine to total lysine ratio of from about 0.8 to about 1.3; (c) leucine in a total leucine to total lysine ratio of from about 1.8 to about 3.0; (d) valine in a total valine to total lysine ratio of from about 0.8 to about 1.4; and (e) methionine and cystine in a total methionine plus cystine to total lysine ratio of from about 0.8 to about 1.7.

9 Claims, No Drawings

COMPOSITIONS AND METHODS FOR INCREASING LEAN MUSCLE MASS AND/OR REDUCING FAT GAIN

CROSS-REFERENCE TO RELATED APPLICATIONS

The present application is a division of U.S. patent application Ser. No. 12/091,757, filed Sep. 15, 2008, which is a national stage entry under 35 U.S.C. 371 of International Patent Application No. PCT/US2006/060249, filed Oct. 26, 2006 which further claims priority to U.S. Provisional Application Ser. No. 60/730,346 filed Oct. 26, 2005, the disclosures of which are incorporated herein by reference.

BACKGROUND OF THE INVENTION

1. Field of the Invention

The present invention relates generally to compositions for increasing lean muscle mass and/or reducing fat gain and particularly to compositions for increasing lean muscle mass and/or reducing fat gain in growing animals. The invention also relates generally to methods for preparing such compositions, methods for using such compositions, articles of manufacture comprising such compositions, and means for communicating information about such compositions, methods, and articles of manufacture.

2. Description of the Prior Art

Growth represents a period of rapid tissue accretion and development, which is reflected primarily by increased needs for energy and essential nutrients, with nutrient and energy needs during growth exceeding those of any other stage of animal's life except lactation. For example, the most rapid growth in dogs and cats occurs during the first 6 months of life, with cats and smaller breeds of dogs reaching adult size by approximately 8 to 12 months of age, medium breeds of dogs—by approximately 12 to 18 months of age, and large breeds of dogs—by approximately 18 to 24 months of age. When they reach maturity, many animals have increased their birth weight by as much as 40- to 50-fold. Thus, an enormous amount of growth and development takes place in a relatively short period of time.

Supplying a balanced diet during growth is crucial for an animal's adequate development and the attainment of normal adult size. Some foods fed to growing animals, and large breed puppies in particular, make the animals look "skinny" or underdeveloped as the animals do not accumulate sufficient lean muscle mass. To make the growing animals appear less skinny, some caregivers overfeed them thus causing the animals gain excess body fat. There is, therefore, a need for compositions and methods that make growing animals less skinny and more developed (i.e., compositions and methods for increasing lean muscle mass and/or reducing fat gain in growing animals).

SUMMARY OF THE INVENTION

It is, therefore, an object of the present invention to provide compositions for increasing lean muscle mass and/or reducing fat gain in growing animals.

It is another object of the invention to provide methods for increasing lean muscle mass and/or reducing fat gain in growing animals.

It is a further object of the invention to provide articles of manufacture comprising a composition of the invention and, optionally, one or more agents for increasing lean muscle mass, reducing fat gain, and/or promoting the health or wellness of growing animals.

It is another object of the invention to provide articles of manufacture comprising two or more ingredients that, when combined, yield a composition of the invention. The articles of manufacture may optionally comprise one or more agents for increasing lean muscle mass, reducing fat gain, and/or improving the health or wellness of growing animals.

It is another object of the invention to provide means for communicating information about the compositions, methods, and articles of manufacture of the invention.

One or more of these and other objects are achieved by using novel compositions that (1) have a total lysine to metabolizable energy ratio of from about 2.5 to about 6 g/Mcal, and (2) comprise (a) arginine in a total arginine to total lysine ratio of from about 1.1 to about 1.6, (b) isoleucine in a total isoleucine to total lysine ratio of from about 0.8 to about 1.3, (c) leucine in a total leucine to total lysine ratio of from about 1.8 to about 3.0, (d) valine in a total valine to total lysine ratio of from about 0.8 to about 1.4, and (e) methionine and cystine in a total methionine plus cystine to total lysine ratio of from about 0.8 to about 1.7. Such compositions are surprisingly effective for increasing lean muscle mass and/or reducing fat gain in growing animals.

Additional objects, features, and advantages of the invention will be apparent to those skilled in the art from reading this patent.

DETAILED DESCRIPTION OF THE INVENTION

In one aspect, the present invention provides a composition for increasing lean muscle mass and/or reducing fat gain in a growing animal. The term "animal" means a human or other animal that can benefit form increasing lean muscle mass and/or reducing fat gain, including avian, bovine, canine, equine, feline, hicrine, murine, ovine, and porcine animals. Preferably, the animal is a canine or feline. The term "growing animal" means an animal that has not reached adult size. In some embodiments, the animal is a member of the order Carnivora. In some such embodiments, the animal is a canine and in other such embodiments the animal is a feline. In some embodiments, the animal is a companion animal. A companion animal can be, for example, an animal of any species that is kept as a pet. A companion animal can also be an animal from a variety of widely domesticated species, for example, dogs (*Canis familiaris*) and cats (*Felis domesticus*) regardless of whether or not the animal is kept solely as a pet. Thus, companion animals include, for example, working dogs, cats kept for working purposes, as well as pet cats and dogs.

The composition has a total lysine to metabolizable energy ratio of from about 2.5 to about 6 g/Mcal. Lysine is an essential amino acid required in an animal's diet for balanced nutrition. Lysine is important in a growing animal's diet because it is generally the limiting amino acid in growth and development. In some embodiments, the composition comprises an amount of lysine that is equal to or higher than the minimum lysine allowance for growth recommended by the Association of American Feed Control Officials ("AAFCO") (i.e., 0.77% on a dry matter basis for dogs (presuming that the energy density of the diet is 3.5 kcal metabolizable energy/g dry matter) and 1.2% on a dry matter for cats (presuming that the energy density of the diet is 4 kcal metabolizable energy/g dry matter)). See 2005 Official Publication of AAFCO Incorporated. The values for the total amount of lysine in the composition (as well as the total amounts of other amino acids) provided herein were determined following amino acid analysis methods 988.15 (regular and sulfur-containing amino acids) and 994.12 (tryptophan) established by the Association of Official Analytical Chemists. See Official Methods of Analysis (1995). Metabolizable energy ("ME") of a composition is the energy available to an animal upon consumption of the composition after subtracting the energy excreted in feces and urine. The AAFCO method for determining ME is shown on page 160 of the in AAFCO, 2005 manual. Metabolizable energy values provided herein were determined following the AAFCO's protocols. The total lysine to metabolizable energy ratio is the total amount of lysine present in the composition relative to the metabolizable energy content of the composition. In some embodiments, particularly those useful with canines, the composition has a total lysine to metabolizable energy ratio of from about 2.5 to about 4.5 g/Mcal. In other embodiments, particularly those useful with felines, the composition has a total lysine to metabolizable energy ratio of from about 3.5 to about 6 g/Mcal.

The composition also comprises (a) arginine in a total arginine to total lysine ratio of from about 1.1 to about 1.6, (b) isoleucine in a total isoleucine to total lysine ratio of from about 0.8 to about 1.3, (c) leucine in a total leucine to total lysine ratio of from about 1.8 to about 3.0, (d) valine in a total valine to total lysine ratio of from about 0.8 to about 1.4, and (e) methionine and cystine in a total methionine plus cystine to total lysine ratio of from about 0.8 to about 1.7. Arginine, isoleucine, leucine, valine, and methionine are essential amino acids required in an animal's diet for balanced nutrition. Cystine is a non-essential sulfur-containing amino acid formed from two molecules of the essential amino acid cysteine. Methionine and cystine are considered together because cystine can provide for a portion of the methionine requirement. In some embodiments, the composition comprises amounts of arginine, isoleucine, leucine, valine, and methionine plus cystine that are equal to or higher than the respective minimum allowances for growth recommended by the AAFCO. In some embodiments, the composition comprises amounts of arginine, isoleucine, leucine, valine, and methionine plus cystine that are up to about 100% higher, up to about 150% higher, up to about 200% higher, up to about 250% higher, up to about 300% higher, up to about 350% higher, up to about 400% higher, or up to about 450% higher than the respective AAFCO minimum allowances for growth. The AAFCO's minimum arginine, isoleucine, leucine, valine, and methionine plus cystine allowances for growth for dogs are 0.62, 0.45, 0.72, 0.48, and 0.53% on a dry matter basis, respectively (presuming that the energy density of the diet is 3.5 kcal ME/g dry matter). The AAFCO's minimum arginine, isoleucine, leucine, valine, and methionine plus cystine allowances for growth for cats are 1.25, 0.52, 1.25, 0.62, and 1.1% on a dry matter, respectively (presuming that the energy density of the diet is 4.0 kcal ME/g dry matter). The total arginine to total lysine ratio is the total amount of arginine present in the composition relative to the total amount of lysine present in the composition. Similarly, the total methionine plus cystine to total lysine ratio is the total amount of methionine and cystine present in the composition relative to the total amount of lysine present in the composition. In some embodiments, the composition comprises (a) arginine in a total arginine to total lysine ratio of from about 1.2 to about 1.4, (b) isoleucine in a total isoleucine to total lysine ratio of from about 0.9 to about 1.1, (c) leucine in a total leucine to total lysine ratio of from about 2.0 to about 2.8, (d) valine in a total valine to total lysine ratio of from about 0.8 to about 1.3, and (e) methionine and cystine in a total methionine plus cystine to total lysine ratio of from about 1.0 to about 1.5.

In some embodiments, the composition further comprises one or more of (a) tryptophan in a total tryptophan to total lysine ratio of from about 0.1 to about 0.5, (b) threonine in a total threonine to total lysine ratio of from about 0.65 to about 1.3, (c) histidine in a total histidine to total lysine ratio of from about 0.3 to about 0.8, and (d) phenylalanine and tyrosine in a total phenylalanine plus tyrosine to total lysine ratio of from about 1.3 to about 2.3. Tryptophan, threonine, histidine, and phenylalanine are essential amino acids required in an animal's diet for balanced nutrition. Tyrosine is a non-essential amino acid. Phenylalanine and tyrosine are considered together because tyrosine can provide for a portion of the phenylalanine requirement. In some embodiments, the composition comprises amounts of tryptophan, threonine, histidine, and phenylalanine plus tyrosine that are equal to or higher than the respective minimum allowances for growth recommended by the AAFCO.

In some embodiments, the composition comprises amounts of tryptophan, threonine, histidine, and phenylalanine plus tyrosine that are up to about 100% higher, up to about 150% higher, up to about 200% higher, or up to about 250% higher than the respective AAFCO minimum allowances for growth. The AAFCO's minimum tryptophan, threonine, histidine, and phenylalanine plus tyrosine allowances for growth for dogs are 0.20, 0.58, 0.22, and 0.89% on a dry matter basis, respectively (presuming that the energy density of the diet is 3.5 kcal ME/g dry matter). The AAFCO's minimum tryptophan, threonine, histidine, and phenylalanine plus tyrosine allowances for growth for cats are 0.25, 0.73, 0.31, and 0.88% on a dry matter, respectively (presuming that the energy density of the diet is 4.0 kcal ME/g dry matter). In some embodiments, the composition comprises one or more of (a) tryptophan in a total tryptophan to total lysine ratio of from about 0.2 to about 0.4, (b) threonine in a total threonine to total lysine ratio of from about 0.8 to about 1.1, (c) histidine in a total histidine to total lysine ratio of from about 0.4 to about 0.7, and (d) phenylalanine and tyrosine in a total phenylalanine plus tyrosine to total lysine ratio of from about 1.6 to about 2.2.

In some embodiments, the composition comprises a food composition. In some embodiments, the food composition meets AAFCO's minimum nutrient level allowances for growth. In some embodiments, the food composition comprises a dry food (i.e., a food containing from about 3 to about 11% water). In other embodiments, the food composition comprises a semi-moist food (i.e., a food containing from about 25 to about 35% water). In some embodiments, the food composition comprises a moist food (i.e., a food containing from about 60 to more than about 87% water). In some embodiments, the food composition comprises a treat, snack, supplement, or partially or fully edible toy.

A composition of the present invention can be prepared by mixing one or more food compositions and optionally one or more additional ingredients such as, for example, amino acids. A composition of the present invention can also be prepared by one or more of the methods discussed in, for example, Small Animal Nutrition, pages 127-46 (2000).

In another aspect, the present invention provides a method for increasing lean muscle mass and/or reducing fat gain in a growing animal. The method comprises feeding the animal a composition discussed above. In some embodiments, a single composition of this invention is fed to the animal until the animal reaches adult size. In other embodiments, different compositions of this invention are fed to the animal for varying time intervals until the animal reaches adult size.

If, for example, a growing animal has severely underdeveloped muscles, it may be desirable to feed a composition of this invention to the animal in conjunction with the administration of one or more agents that can help increase the animal's lean muscle mass. Similarly, if a growing animal has excess fat, it may be desirable to feed a composition of the present invention to the animal in conjunction with the administration of one or more agents that can help the animal reduce fat gain. In addition, if a growing animal suffers from one or more diseases, it may be needed to feed a composition of the present invention to the animal in conjunction with the administration of one or more agents that can help promote the animal's health.

Thus, in some embodiments, the method of the invention further comprises administering to the animal one or more agents for increasing lean muscle mass, reducing fat gain, and/or promoting the health or wellness of the animal. Health of an animal refers to the absence of disease or infirmity. Wellness refers to the complete physical, mental, and social wellbeing of the animal, not merely the absence of infirmity. The term "in conjunction" means that an agent is administered to the animal either together with a composition of the present invention or separately from the composition at the same or different frequency via the same or different administration route and either at about the same time as the composition or periodically. "About at the same time" generally means that an agent is administered to an animal when a composition of the present invention is fed to the animal or within about 72 hours of feeding the composition to the animal. "Periodically" generally means that an agent is administered to an animal following a dosage schedule suitable for administering that agent while a composition of the present invention is fed to the animal routinely as appropriate for that animal. Thus, the term "in conjunction" specifically includes situations when an agent is administered to an animal for a prescribed period of time while a composition of the present invention is fed to the animal until it reaches normal adult size. If two or more agents are to be administered to an animal, the dosage schedule and route of administration for each agent may vary. In addition, as discussed above, one composition of the present invention may be substituted with another composition of the present invention while a specific agent is administered to the animal.

In some embodiments, the agent for increasing lean muscle mass and/or reducing fat gain comprises carnitine. Carnitine, or L-carnitine, is a vitamin-like compound that is synthesized in the body from lysine and methionine. Carnitine attaches to long-chain fatty acids and transports them into cellular mitochondria where the fatty acids are broken down through oxidation and converted to energy for all tissues including the skeletal muscles, heart, and liver. Through this process, carnitine helps reduce storage of body fat and the amount of fat in the blood stream. In some embodiments, the agent for increasing lean muscle mass and/or reducing fat gain comprises chromium. Chromium is a trace element and a cofactor for insulin that regulates the metabolism of proteins, fats, and carbohydrates. Chromium helps lose body fat, retain and build lean body mass, lower elevated blood sugar, and reduce blood cholesterol levels. Administration of chromium in the form of chromium picolinate or chromium polynicotinate can help increase the absorption of chromium in the digestive system.

An agent for promoting health or wellness can, for example, improve an animal's cognitive functions or the appearance and thickness of an animal's hair coat, or can ameliorate or treat a disease that the animal suffers from. In some embodiments, the agent for promoting health or wellness comprises one or more antioxidants. An antioxidant is a nutrient or non-nutrient substance that prevents formation of, or quenches, free radicals. Vitamin E, for example, works in conjunction with glutathione peroxidase to protect cells against the adverse effects of reactive oxygen and other free radicals that initiate the oxidation of polyunsaturated membrane phospholipids. Vitamin E can be administered in the form of an $\alpha$-, $\beta$-, $\gamma$-, or $\delta$-tocopherol, $\alpha$-, $\beta$-, $\gamma$-, or $\delta$-tocotrienol, or a mixture of any of those isomeric forms. Another antioxidant, vitamin C, protects against free radical damage induced by the oxidative burst of neutrophils and stimulates the phagocytic effect of leukocytes, thus playing a role in immune function. Vitamin C (and L-ascorbic acid in particular) can be administered, for example, in the form of a salt or ester such as sodium, calcium, zinc, or ferrous salt or stearate or palmitate ester. In some embodiments, the agent for promoting health or wellness comprises one or more essential fatty acids such as, for example, omega-6 or omega-3 fatty acids. Omega-6 essential fatty acids include, for example, linoleic acid and arachidonic acid. Omega-3 essential fatty acids include, for example, alpha-linolenic acid, eicosapentaenoic acid, and docosahexaenoic acid. Essential fatty acids serve as substrates that may be metabolized to form important, biologically active compounds. Arachidonic acid, gamma-linolenic acid, and eicosapentaenoic acid act as precursors for the synthesis of eicosanoids, an important group of immunoregulatory molecules that function as local hormones and mediators of inflammation. Linoleic acid incorporates into the ceramides of the epidermal cornified envelope, which serves an essential barrier function to prevent loss of water and other nutrients from the skin. Essential fatty acid may be used in the form of various derivatives, for example, salts of inorganic and organic acids, phospolipid esters, ethers, and sterol derivatives. Linoleic and linolenic acids can be used as, for example, phosphatidal choline esters, phosphatidal ether, and sipolsterol ester.

In another aspect, the present invention provides an article of manufacture in the form of a kit comprising a composition of the present invention as discussed above. In some embodiments, the kit further comprises one or more agents for increasing lean muscle mass, reducing fat gain, and/or promoting the health or wellness of a growing animal. In some embodiments, the kit further comprises instructions for at least one of (1) feeding a composition of the present invention to a growing animal, (2) administering an agent for increasing lean muscle mass, increasing bone density, reducing body fat, and/or promoting the health or wellness of a growing animal in conjunction with a composition of the present invention.

In another aspect, the present invention provides an article of manufacture in the form of a kit comprising two or more ingredients that, when combined together and optionally with additional ingredients that are not a part of the kit, yield a composition of the present invention. In some embodiments, the kit further comprises one or more agents for increasing lean muscle mass, reducing fat gain, and/or promoting the health or wellness of a growing animal. In some embodiments, the kit further comprises instructions for at least one of (1) making a composition of the present invention by combining the two or more ingredients and, optionally, additional ingredients that are not a part of the kit, (2) feeding the composition to a growing animal, and (3) administering one or more agents for increasing lean muscle mass, increasing bone density, reducing body fat, and/or promoting the health or wellness of a growing animal in conjunction with the composition.

In some embodiments, the kit comprises in separate containers in a single package or in separate containers in a virtual package, as appropriate a composition of the present invention or two or more ingredients, that, when combined, yield a composition of the present invention, and at least one of (1) instructions for feeding the composition to a growing animal, (2) instructions for making a composition of the present invention by combining the two or more ingredients, (3) one or more agents for increasing lean muscle mass, reducing fat gain, and/or promoting the health or wellness of a growing animal, and (4) instructions for administering the agents in conjunction with the composition. The term "single package" generally means that the components of a kit are physically associated in or with one or more containers and considered as a unit of manufacture, distribution, sale, or use. Containers include, but are not limited to, bags, boxes, bottles, shrink wrap packages, stapled or otherwise fixed components, or combinations thereof. A single package can be, for example, containers or individual food compositions physically associated such that they are considered a unit for manufacture, distribution, sale, or use. The term "virtual package" generally means that the components of a kit are associated by directions on one or more physical or virtual kit components instructing the user how to obtain additional components, e.g., in a bag containing one component and directions instructing the user to go to a website, contact a recorded message, view a visual message, or contact a caregiver to obtain instructions on how to use the kit. When the kit comprises a virtual package, the kit is limited to instructions in a virtual environment with one or more physical kit components.

In another aspect, the present invention provides a means for communicating information about or instructions for one or more of (1) using a composition of the present invention for increasing lean muscle mass and/or reducing fat gain in a growing animal, (2) using a composition of the present invention in conjunction with one or more agents for increasing lean muscle mass, reducing fat gain, and/or promoting the health or wellness of a growing animal, and (3) using a kit of the present invention for increasing lean muscle mass and/or reducing fat gain in a growing animal comprising a document, digital storage media, optical storage media, audio presentation, or visual display containing the information or instructions. In certain embodiments, the communicating means comprises a document, digital storage media, optical storage media, audio presentation, or visual display containing the information or instructions. Preferably, the communication means is a displayed web site or a brochure, product label, package insert, advertisement, or visual display containing such information or instructions. Useful information or instructions include, for example, (1) information and instructions how to use a composition, method, or kit of the present invention and (2) contact information for animal caregivers if they have a question about the invention and its uses.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly indicates otherwise. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of this invention. Although any methods and materials similar or equivalent to those described herein can be used in the practice of the present invention, the preferred methods, devices, and materials are described herein.

All references mentioned herein are incorporated herein by reference to the extent allowed by law for the purpose of describing and disclosing the compositions, compounds, methods, and similar information reported herein that might be used in the present invention. However, nothing herein is to be construed as an admission that the invention is not entitled to antedate such disclosure by virtue of prior invention.

EXAMPLES

This invention can be further illustrated by the following example, although it will be understood that the example is included merely for purposes of illustration and is not intended to limit the scope of the invention unless otherwise specifically indicated.

Example 1

Twenty-one (21) large breed puppies were switched to food A at weaning (i.e., at 2 months of age) to be fed food A until they are 18 months old. Similarly, 14 large breed puppies were switched to food B at weaning to be fed food B until they are 18 months old. Both food A and food B met the AAFCO's minimum nutrient allowances for growth. The results from the nutrient analysis of both foods are presented in Table 1.

TABLE 1

Nutrient Analysis of Food A and Food B

| Nutrient | Units | Food A | Food B |
|---|---|---|---|
| Protein | % DMB | 32.2 | 29.2 |
| Fat | % DMB | 17.2 | 15.2 |
| Crude Fiber | % DMB | 2.60 | 2.06 |
| Calcium | % DMB | 1.15 | 0.88 |
| Phosphorus | % DMB | 0.92 | 0.76 |
| Calcium:Phosphorus ratio | — | 1.25 | 1.16 |
| Sodium | % DMB | 0.5 | 0.44 |
| Potassium | % DMB | 0.76 | 0.80 |
| Magnesium | % DMB | 0.12 | 0.12 |
| Chloride | % DMB | 1.14 | 1.00 |
| Zinc | ppm | 195 | 260 |
| Manganese | ppm | 101 | 51 |
| Carnitine | ppm | ~300 | none |
| Lysine | % DMB | 1.33 | 1.77 |
| (Methionine + Cystine):Lysine ratio | — | 1.31 | 0.59 |
| Tryptophan:Lysine ratio | — | 0.20 | 0.18 |
| Threonine:Lysine ratio | — | 0.87 | 0.60 |
| Arginine:Lysine ratio | — | 1.25 | 0.97 |
| Isoleucine:Lysine ratio | — | 0.91 | 0.68 |
| Valine:Lysine ratio | — | 1.12 | 0.87 |
| Leucine:Lysine ratio | — | 2.60 | 1.36 |
| Histidine:Lysine ratio | — | 0.49 | 0.39 |
| (Phenylalanine + Tyrosine):Lysine ratio | — | 1.95 | 1.14 |
| Metabolizable Energy (ME) | kcal/kg | 4000 | 4138 |
| Lysine:ME ratio | g/Mcal | 3.33 | 4.13 |

DMB = dry matter basis

Lean and fat tissue measurements of all puppies were performed by dual energy x-ray absorptiometry at weaning and when the puppies were 5 months old. The results are presented in Table 2 (the initial component (day 0 on food A or food B) was used as a covariate in the statistical model). Namely, the puppies fed food A gained more lean tissue but less fat tissue than the puppies fed food B.

TABLE 2

Dual Energy X-ray Absorptiometry Data at 5 Months of Age

| Item | Units | Food A | Food B | p-value |
|---|---|---|---|---|
| Lean tissue | g | 12970 | 12290 | 0.17 |
| Fat tissue | g | 3469 | 4803 | 0.01 |
| Body weight | g | 17080 | 17464 | 0.65 |
| Lean | % of body weight | 76.31 | 70.59 | 0.01 |
| Fat | % of body weight | 20.55 | 26.37 | 0.01 |
| Lean gain | g | 8444.02 | 7634.85 | 0.11 |
| Fat gain | g | 2969.79 | 4183.96 | 0.11 |
| Total weight gain | kg | 11.842 | 12.238 | 0.59 |

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the invention are possible in light of the above teachings. It is therefore to be understood that within the scope of the appended claims the invention may be practiced otherwise than as specifically described.

What is claimed is:

1. A composition for increasing lean muscle mass and/or reducing body fat in a growing animal wherein the composition has a total lysine to metabolizable energy ratio of from about 2.5 to about 6 g/Mcal and comprises:
   a. arginine in a total arginine to total lysine ratio of from about 1.1 to about 1.6;
   b. isoleucine in a total isoleucine to total lysine ratio of from about 0.8 to about 1.3;
   c. leucine in a total leucine to total lysine ratio of from about 1.8 to about 3.0;
   d. valine in a total valine to total lysine ratio of from about 0.8 to about 1.4;
   e. methionine and cystine in a total methionine plus cystine to total lysine ratio of from about 0.8 to about 1.7;
   f. protein in an amount of at least about 29%; and
   g. fat in an amount greater of at least about 15%;
   wherein the growing animal is a canine or feline.

2. The composition of claim 1 wherein the composition further comprises:
   a. tryptophan in a total tryptophan to total lysine ratio of from about 0.1 to about 0.5;
   b. threonine in a total threonine to total lysine ratio of from about 0.65 to about 1.3;
   c. histidine in a total histidine to total lysine ratio of from about 0.3 to about 0.8; and
   d. phenylalanine and tyrosine in a total phenylalanine plus tyrosine to total lysine ratio of from about 1.3 to about 2.3.

3. A kit for increasing lean muscle mass and/or reducing fat gain in a growing animal comprising two or more ingredients that, when combined together and optionally with additional ingredients that are not a part of the kit, yield a composition that has a total lysine to metabolizable energy ratio of from about 2.5 to about 6 g/Mcal and comprises:
   a. arginine in a total arginine to total lysine ratio of from about 1.1 to about 1.6;
   b. isoleucine in a total isoleucine to total lysine ratio of from about 0.8 to about 1.3;
   c. leucine in a total leucine to total lysine ratio of from about 1.8 to about 3.0;
   d. valine in a total valine to total lysine ratio of from about 0.8 to about 1.4;
   e. methionine and cystine in a total methionine plus cystine to total lysine ratio of from about 0.8 to about 1.7;
   f. protein in an amount of at least about 29%; and
   g. fat in an amount of at least about 15%;
   wherein the growing animal is a canine or feline.

4. The kit of claim 3 wherein the kit further comprises one or more agents for increasing lean muscle mass, reducing fat gain, and/or promoting the health or wellness of a growing animal and optionally one or more of (1) instructions for making a composition of the present invention by combining the two or more ingredients and, optionally, additional ingredients that are not a part of the kit, (2) instructions for feeding the composition to the animal, and (3) instructions for administering the agents in conjunction with the composition.

5. A kit for increasing lean muscle mass and/or reducing fat gain in a growing animal comprising in separate containers in a single package or in separate containers in a virtual package, as appropriate, the composition of claim 1 or two or more ingredients, that, when combined together and optionally with additional ingredients that are not a part of the kit, yield a composition of claim 1, and at least one of (1) instructions for feeding the composition to the animal, (2) instructions for making a composition of the present invention by combining the two or more ingredients, (3) one or more agents for increasing lean muscle mass, reducing fat gain, and/or promoting the health or wellness of a growing animal, and (4) instructions for administering the agents in conjunction with the composition.

6. A means for communicating information about or instructions for (1) using a composition of claim 1 for increasing lean muscle mass and/or reducing fat gain in a growing animal, or (2) using one or more agents for increasing lean muscle mass, reducing fat gain, and/or promoting the health or wellness of a growing animal in conjunction with a composition of claim 1, the means comprising a document, digital storage media, audio presentation, or visual display containing the information or instructions.

7. The means of claim 6 selected from the group consisting of brochure, product label, package insert, advertisement, displayed web site, and visual display.

8. A means for communicating information about or instructions for using a kit of claim 5, the means comprising a document, digital storage media, audio presentation, or visual display containing the information or instructions.

9. The means of claim 8 selected from the group consisting of brochure, product label, package insert, advertisement, displayed web site, and visual display.

* * * * *